(12) United States Patent
Movassaghi et al.

(10) Patent No.: US 8,045,677 B2
(45) Date of Patent: Oct. 25, 2011

(54) SHIFTING AN OBJECT FOR COMPLETE TRAJECTORIES IN ROTATIONAL X-RAY IMAGING

(75) Inventors: Babak Movassaghi, Denver, CO (US); Robert Manzke, Cambridge, MA (US); Joel Alberto Garcia, Denver, CO (US)

(73) Assignee: Koninklijke Philips Electronics N V Eindhoven (NL)

( * ) Notice: Subject to any disclaimer, the term of this patent is extended or adjusted under 35 U.S.C. 154(b) by 103 days.

(21) Appl. No.: 12/441,613

(22) PCT Filed: Sep. 17, 2007

(86) PCT No.: PCT/IB2007/053744
§ 371 (c)(1),
(2), (4) Date: Aug. 20, 2009

(87) PCT Pub. No.: WO2008/038176
PCT Pub. Date: Apr. 3, 2008

(65) Prior Publication Data
US 2010/0027742 A1    Feb. 4, 2010

(30) Foreign Application Priority Data
Sep. 25, 2006 (EP) .................... 06121190

(51) Int. Cl.
*G01N 23/04* (2006.01)
*G01N 23/083* (2006.01)
(52) U.S. Cl. ............. 378/20; 378/62; 378/196; 378/205
(58) Field of Classification Search .................... 378/20, 378/62, 196, 205
See application file for complete search history.

(56) References Cited

U.S. PATENT DOCUMENTS

| | | | |
|---|---|---|---|
| 4,789,929 A | 12/1988 | Nishimura et al. | |
| 5,195,114 A * | 3/1993 | Sairenji et al. | 378/40 |
| 5,930,328 A | 7/1999 | Nakamura et al. | |
| 6,246,742 B1 * | 6/2001 | Besson et al. | 378/8 |
| 6,764,217 B2 * | 7/2004 | Yasuda et al. | 378/205 |
| 7,313,215 B2 * | 12/2007 | Hsieh et al. | 378/15 |
| 7,486,759 B2 * | 2/2009 | Suzuki et al. | 378/4 |
| 2002/0090058 A1 | 7/2002 | Yasuda et al. | |
| 2003/0069499 A1 | 4/2003 | Lienard et al. | |
| 2004/0184583 A1 | 9/2004 | Nagamine et al. | |

(Continued)

FOREIGN PATENT DOCUMENTS
DE  19909527 A1  9/2000
(Continued)

*Primary Examiner* — Edward Glick
*Assistant Examiner* — Thomas R Artman (57) ABSTRACT

It is described a method for acquiring a series of two-dimensional X-ray attenuation data of an object under examination (310) by means of an X-ray imaging apparatus (100) having a rotatable scanning unit (301). In order to increase the angular range of the scanning unit (301), when a region of interest (HOa) located not in the center of the object (310) is examined the object under examination (310) is shifted such that the region of interest is temporarily positioned outside the center of rotation. By coupling the rotational movement of the scanning unit (301) with the translative movement of the object (310) in a synchronized manner a collision between the scanning unit (301) and the object (310) can be effectively avoided. By employing an automated motorized object table (312) a precise pre-determined movement of the object (310) can be achieved during the data acquisition. By using an appropriate phantom based calibration procedure carried out with the same table movements known three-dimensional reconstruction algorithm can be directly applied in order to generate a three-dimensional representation of the region of interest (110a).

20 Claims, 7 Drawing Sheets

U.S. PATENT DOCUMENTS

| | | |
|---|---|---|
| 2005/0177044 A1 | 8/2005 | Rubin et al. |
| 2005/0218341 A1 | 10/2005 | Saracen et al. |
| 2005/0256390 A1 | 11/2005 | Laux et al. |
| 2009/0283682 A1* | 11/2009 | Star-Lack et al. .......... 250/363.1 |
| 2010/0246755 A1* | 9/2010 | Suzuki et al. ................ 378/11 |

FOREIGN PATENT DOCUMENTS

| | | |
|---|---|---|
| FR | 2641180 A1 | 7/1990 |
| JP | 2006003200 A | 1/2006 |
| WO | 98041194 A1 | 2/1998 |
| WO | 2005039472 A2 | 5/2005 |
| WO | 2005099578 A2 | 10/2005 |

* cited by examiner

SHIFTING AN OBJECT FOR COMPLETE TRAJECTORIES IN ROTATIONAL X-RAY IMAGING

The present invention relates to the field of rotational X-ray imaging. In particular the present invention relates to a method for acquiring a series of two-dimensional X-ray attenuation data of an object under examination by means of an X-ray imaging apparatus having a rotatable X-ray scanning unit. Thereby, the rotatable X-ray scanning unit comprises an X-ray source, which is adapted for emitting a radiation beam, and an X-ray detector, which is adapted for detecting the radiation beam after the radiation beam has passed the object under examination.

The present invention further relates to a data processing device and to a medical X-ray imaging apparatus for acquiring a series of two-dimensional X-ray attenuation data of an object under examination by means of a rotatable X-ray scanning unit.

Furthermore, the present invention relates to a computer-readable medium and to a program element having instructions for executing the above-mentioned method for acquiring a series of two-dimensional X-ray attenuation data of an object under examination by means of a rotatable X-ray scanning unit.

In the recent years three-dimensional rotational angiography has been introduced where a C-arm X-ray imaging system rotates around the patient while acquiring projection images from a region of interest located within an object under examination. The most common applications are currently in the field of interventional neurology, with a growing interest in the field of interventional cardiology. In both cases contrast filled agent is injected into the vessel structure of a patient under examination while acquiring two-dimensional (2D) X-ray angiograms during a rotational run of the C-arm system. The acquired projection images can then be used for diagnostic purposes, and/or can be utilized to make a three-dimensional (3D) reconstruction of the region of interest.

In order to limit the radiation exposure of a patient under examination to the designated region of interest within the body of the patient there are known various way to perform an appropriate positioning of the patient with respect to a beam of X-rays or even to a beam of particles. Thereby, a beam of particles is typically used for treating carcinogenic tissue. By contrast thereto, an X-ray beam may be used both for diagnostic and for therapeutic purposes.

US2004/0184583 A1 discloses a device for positioning a patient relative to a particle beam, which is used for irradiating a tumor in the body of the patient. The patient positioning device comprises (a) an X-ray emission device for emitting X-rays along a beam line in front of a particle beam irradiation section, (b) an X-ray image capturing device for receiving the X-rays and processing an X-ray image and (c) a display unit for displaying a current image of the tumor in accordance with a processed image signal. The patient positioning device further comprises (d) a display unit for displaying a reference X-ray image of the tumor, which is prepared in advance, and (e) a positioning data generator for executing pattern matching between a first comparison area being a part of the reference X-ray image and a second comparison area being a part of the current image. Thereby, data for positioning the patient by moving a patient's couch are produced during the particle beam irradiation.

US2005/0256390 A1 discloses a medical imaging examination apparatus with an automatic patient positioning. The medical imaging examination apparatus comprises (a) an image acquisition device, (b) a patient bed, (c) a control device to control the image acquisition means and to move the patient bed as well as (d) a monitor connected with the control device for image output. In an examination image of the patient shown on the monitor that has been acquired with a first patient bed position with the imaging medical examination apparatus, an operator can designate on the monitor a desired new patient bed position for implementation of further examinations. The control device automatically determines the position data of the defined bed position and controls movement of the bed dependent on the determined position data such that the bed subsequently assumes the desired new position.

US2005/0218341 A1 discloses a method of positioning a treatment target to the iso-center of a treatment system for irradiating a tumor of a patient with a particle beam being generated by a linear particle accelerator. The method includes a simulation process and a real treatment positioning process. The simulation process includes positioning the treatment target to an iso-center of a simulation system and marking intersection points where laser beams intersect with an exterior of the patient's body. The real treatment positioning process includes (a) determining the position of the intersection points marked on the exterior of the patient body, (b) determining a treatment position for positioning the patient such that the treatment target is aligned with the iso-center of the real treatment system and (c) positioning the patient to the treatment position.

With respect to rotational X-ray imaging by means of a C-arm X-ray imaging system a proper positioning of the object under examination is essential in order to allow for a high quality 3D reconstruction of the object. Thereby, a region of interest within the object under examination is positioned within the center of rotation of the C-arm system. In particular when a region of interest is examined, which region is not located in the center of the object, a precise positioning of the object is essential in order to avoid a collision between parts of the C-arm system and the object.

There may be a need for providing a method for acquiring a series of two-dimensional X-ray attenuation data of an object under examination by means of an X-ray imaging apparatus having a rotatable X-ray scanning unit, which method allows for a proper positioning of the object under examination during the X-ray data acquisition at different projection angles.

This need may be met by the subject matter according to the independent claims. Advantageous embodiments of the present invention are described by the dependent claims.

According to a first aspect of the invention there is provided a method for acquiring a series of two-dimensional X-ray attenuation data of an object under examination by means of an X-ray imaging apparatus having an X-ray scanning unit. The provided method comprises the steps of (a) rotating the X-ray scanning unit around a rotational axis such that the object under examination is scanned under different projection angles, and (b) moving the object under examination relative to the rotational axis, wherein the movement of the object under examination is coupled to the rotation of the X-ray scanning unit.

This aspect of the invention is based on the idea that a predetermined translative movement of the object during the X-ray data acquisition allows to compensate for spatial restrictions which may be caused if the object under examination is originally not located in the center respectively the iso-center of the X-ray imaging apparatus. Thereby, a collision between the scanning unit and an outer part of the object being located outside the iso-center may be avoided. Without such a translative shift of the object such a collision might occur at a certain angular position of the scanning unit. The iso-center is defined by the intersection of the rotational axis and the optical axis of the scanning unit.

The employed X-ray scanning unit comprises an X-ray source such as an X-ray tube and an X-ray detector, preferably a flat detector having a spatial resolution. The X-ray source and the X-ray detector may be attached to a gantry such as a holder of a C-arm. However, the X-ray source and the X-ray detector may also be attached to a self-contained holder which is used e.g. in computed tomography systems.

The described method provides the advantage that the angular range of the X-ray scanning unit might be increased in particular for voluminous objects, which are originally located outside the iso-center of the X-ray imaging apparatus. An original positioning of the object under examination outside the iso-center is in particular beneficial when a region of interest within the object is supposed to be examined, which region of interest is located not in the center of the object. This allows for a proper positioning of the region of interest within the iso-center of the X-ray scanning unit.

By shifting the object such that the region of interest is temporarily positioned outside the center of rotation, a collision between the scanning unit and the object can be effectively avoided and the possible angular range of the scanning unit can be widened. Of course, by shifting the object under examination the region of interest is at least temporarily not located in the iso-center. However, compared to a collision-restricted range of projection angles, additional X-ray attenuation data, which have been acquired with the region of interest being located offset from the iso-center, provide nonetheless further useful information about the region of interest. Of course, this requires a sufficient large cross sectional area of the X-radiation beam extending from the X-ray source to the X-ray detector at the iso-center such that at least eccentric X-rays penetrate the region of interest. This condition can be fulfilled easily by employing a flat X-ray detector having a comparatively large area.

According to an embodiment of the invention the object under examination is moved in a direction transversal to the rotational axis. In this respect it has to be mentioned that the direction of the transversal movement of the object may be either inclined or perpendicular to the rotational axis. Anyway, it is important that the object or at least a part of the object is moved out of the iso-center of the X-ray imaging apparatus.

According to an embodiment of the invention the method further comprises the steps of (a) rotating the X-ray scanning unit to a first predefined angular position, whereby the object under examination is located at a first translative position, (b) moving the object under examination from the first translative position to a second translative position, and (c) rotating the X-ray scanning unit to a second predefined angular position. Such a horizontal shuttle movement after reaching a certain angular position may provide the advantage that in a wide angular range the data acquisition may be carried out with the object being located at one and the same translative position.

According to a further embodiment of the invention the method further comprises the steps of (a) moving the object under examination from the second translative position back to the first translative position, and (b) further rotating the X-ray scanning unit. This may provide the advantage that the object is located at the second translative position only when a collision between the X-ray scanning unit and the object has to be avoided. For angular positions of the scanning unit, where there is no risk for a collision, the object under examination may be located at the original first translative position such that a region of interest within the object may be located in the iso-center even if the this region of interest is located off-center in the whole object.

Preferably, the further rotation is carried out until the X-ray scanning unit is situated again in the first predefined angular position. Thereby, a complete 360° cycle of the scanning unit including an intermediate translative shift of the object is defined. This may provide the advantage that the object under examination may be scanned with a plurality of rotational cycles. Thereby, by combining the X-ray attenuation data acquired at different revolutions the quality of the corresponding X-ray images obtained at different projection angles may be enhanced.

It has to be mentioned that of course during one rotational cycle the object might also be shifted stepwise to a variety of different second translative positions. Thereby, for each angular position of the X-ray scanning unit the shift of the object is solely as big as it is necessary to avoid a collision between the scanning unit and the object.

According to a further embodiment of the invention the movement of the object under examination is carried out during a time period in which the rotation of the X-ray scanning unit is temporarily stopped. This means that the data acquisition is carried out exclusively at discrete translative positions of the object under examination. This may provide the advantage that images at different projection angles can be compared comparatively easy because only a limited number of different object positions have to be considered.

A further advantage may be provided if the X-ray projection data obtained at various different angular positions are combined in order to reconstruct a three-dimensional (3D) representation of the object under examination. By momentarily stopping the rotation of the X-ray scanning unit a corresponding reconstruction procedure is more reliable because the number of different translative object positions is limited such that the overall uncertainty about of the correct translative position is reduced.

According to an alternative embodiment of the invention the movement of the object under examination is carried out during a time period in which the X-ray scanning unit is rotated from the first predefined angular position to the second predefined angular position. This may provide the advantage that it is not necessary to stop the data acquisition during the translative movement of the object under examination such that the overall acquisition time can effectively be reduced.

According to a further embodiment of the invention the object under examination is situated at a support element, which support element is coupled to a drive means for generating the movement of the object under examination. Preferably, the support element is a table, which may be moved at least along a direction transversal to the rotational axis. However, the table may also be driven along further directions such that a proper positioning of the object under examination may be achieved. Since patient tables used in medical X-ray imaging apparatuses are typically movable in all three directions is space, the described data acquisition method can be easily implemented in current used medical X-ray imaging apparatuses.

By using an automated motorized table a precise positioning of the object can be achieved. This may provide the advantage that the uncertainty of the exact object position is reduced such that projection data acquired both under different angular positions of the scanning unit and at different translative positions of the object may be combined by means of a reliable reconstruction procedure leading to a 3D representation of the object under examination.

According to a further embodiment of the invention the object under examination is at least a region of interest of a body of a patient. This has the advantage that in medical X-ray imaging the described method may be used to effectively increase the angular range of an X-ray imaging apparatus such as a C-arm system in particular when thick patients have to be examined.

According to a further embodiment of the invention the region of interest is an organ of the patient, which organ is located off-center within the body of the patient, in particular the region of interest is the heart of the patient.

Preferably, during a first phase of the X-ray data acquisition, when the patient's body is located within the first translative position, the organ is located in the iso-center of the medical X-ray imaging apparatus. This means that the patient's body as a whole is located off-center. In order to avoid a collision between the scanning unit and the patient's body at a subsequent angular position of the scanning unit, the patient is moved in due time to the second translative position. Thereby, the patient's body as a whole is moved at least towards the iso-center whereby the organ of the patient is moved away from the iso-center. This allows for a further rotation of the X-ray scanning unit.

At this point it has to be mentioned that the size of the flat X-ray detector of the scanning unit has to be big enough in order to ensure, that the off-center organ is still within the cross section of the X-ray beam extending between the X-ray source and the X-ray detector. If this would be not the case the increase of the collision free angular range of the scanning unit would not be useful because no further X-ray attenuation data of the organ can be acquired. However, in most current used C-arm systems the cross section of the X-ray beam is big enough in order to allow also an X-ray imaging of organs, which are not located in the iso-center of the employed C-arm system.

According to a further embodiment of the invention the method further comprises the step of inserting a contrast agent into the body of a patient. This may provide the advantage that the internal vessel structure of the patient may be illustrated very clearly by means of a rotational angiography. Due to the increased collision free angular range of the scanning unit the known problem of foreshortening the length of vessel sections, which are oriented almost parallel to the optical axis of the X-ray scanning unit, is eliminated. When using the described method it will be possible to acquire X-ray images also at other angular positions, wherein these vessel sections are oriented at least almost perpendicular to the optical axis of the X-ray scanning unit.

According to a further embodiment of the invention the method further comprises the step of reconstructing a three-dimensional representation of the object under examination based on the acquired series of two-dimensional X-ray attenuation data, whereby the movement of the object under examination is taken into account. Thereby, the movement of the object under examination causes a shift of the relevant attenuation data on the flat X-ray detector. Of course, this spatial data shift depends on the angle $\theta$ between the direction of the translative movement and the detector plane. Specifically, the spatial data shift $\Delta S$ is given by the expression $\Delta S = \Delta x \cdot \cos \theta$, wherein $\Delta x$ is the moving distance of the object under examination.

According to a further embodiment of the invention the method further comprises the step of carrying out a calibration procedure for registering the movement of the object under examination with the rotation of the X-ray scanning unit. Preferably, the calibration procedure is carried out by using an appropriate phantom in order to register the translative movement of the phantom respectively the object with the rotational movement of X-ray scanning unit. Of course, both the movement of the object under examination and the trajectory of the X-ray scanning unit have to be reproducible such that the real data acquisition can be carried out under the same conditions, which conditions have been available already for calibration procedure.

In case of a accomplishing a 3D reconstruction of the object under examination this may provide the advantage that the motion compensation of the acquired projection data due to the translative movement of the object and the acquired X-ray attenuation data can be directly applied to commercially utilized 3D reconstruction algorithms.

According to a further aspect of the invention there is provided a data processing device for acquiring a series of two-dimensional X-ray attenuation data of an object under examination by means of an X-ray imaging apparatus having a rotatable X-ray scanning unit. The data processing device comprises (a) a data processor, which is adapted for controlling exemplary embodiments of the above-described method, and (b) a memory for storing the series of acquired two-dimensional X-ray attenuation data.

According to a further aspect of the invention there is provided a medical X-ray imaging apparatus for acquiring a series of two-dimensional X-ray attenuation data of an object under examination. The medical X-ray imaging apparatus is in particular a so-called C-arm system, which comprises an X-ray scanning unit being rotatable around a rotational axis. The X-ray scanning unit itself comprises an X-ray source, which is adapted for emitting a radiation beam, and an X-ray detector, which is adapted for detecting the radiation beam after the radiation beam has passed the object under examination. The medical X-ray imaging apparatus further comprises the above described a data processing device.

According to an embodiment of the invention the medical X-ray imaging apparatus further comprises (a) a support element for supporting the object under examination and (b) a drive means, which is coupled to the support element and which is adapted for generating the transversal movement of the object under examination. As has already been mentioned above, the support element may be a movable table, which allows for a precise and reproducible positioning of the object under examination.

According to a further embodiment of the invention the medical X-ray imaging apparatus further comprises a control unit, which is coupled to the drive means and which is adapted to control the movement of the support element. This has the advantage that a fully automated motorized support element may be realized such that a precise and reproducible positioning of the object can be achieved. Preferably, the control unit is also directly or indirectly coupled to a motor for generating the rotational movement of the scanning unit. Thereby, a perfect synchronization between the rotational movement of the scanning unit and the translative movement of the object may be realized.

It has to be mentioned that the control unit may be realized by means of a computer program respectively software. However, the invention may also be realized by means of one ore more specific electronic circuits respectively hardware. Furthermore, the invention may also be realized in a hybrid form, i.e. in a combination of software modules and hardware modules.

According to a further aspect of the invention there is provided a computer-readable medium on which there is stored a computer program for acquiring a series of two-dimensional X-ray attenuation data of an object under examination by means of an X-ray imaging apparatus having a rotatable X-ray scanning unit. The computer program, when being executed by a data processor, is adapted for controlling exemplary embodiments of the above-described method.

According to a further aspect of the invention there is provided a program element for acquiring a series of two-dimensional X-ray attenuation data of an object under examination by means of an X-ray imaging apparatus having a rotatable X-ray scanning unit. The program element, when being executed by a data processor, is adapted for controlling exemplary embodiments of the above-described method.

The computer program element may be implemented as a computer readable instruction code in any suitable programming language, such as, for example, JAVA, C++, and may be stored on a computer-readable medium (removable disk, volatile or non-volatile memory, embedded memory/processor, etc.). The instruction code is operable to program a computer or other programmable device to carry out the intended functions. The computer program may be available from a network, such as the WorldWideWeb, from which it may be downloaded.

It has to be noted that embodiments of the invention have been described with reference to different subject matters. In particular, some embodiments have been described with reference to method type claims whereas other embodiments have been described with reference to apparatus type claims. However, a person skilled in the art will gather from the above and the following description that, unless other notified, in addition to any combination of features belonging to one type of subject matter also any combination between features relating to different subject matters, in particular between features of the method type claims and features of the apparatus type claims is considered to be disclosed with this application.

The aspects defined above and further aspects of the present invention are apparent from the examples of embodiment to be described hereinafter and are explained with reference to the examples of embodiment. The invention will be described in more detail hereinafter with reference to examples of embodiment but to which the invention is not limited.

FIG. 1b shows a perspective view of the C-arm depicted in FIG. 1a.

The illustration in the drawing is schematically. It is noted that in different figures, similar or identical elements are provided with the same reference signs or with reference signs, which are different from the corresponding reference signs only within the first digit.

Figure 1A:
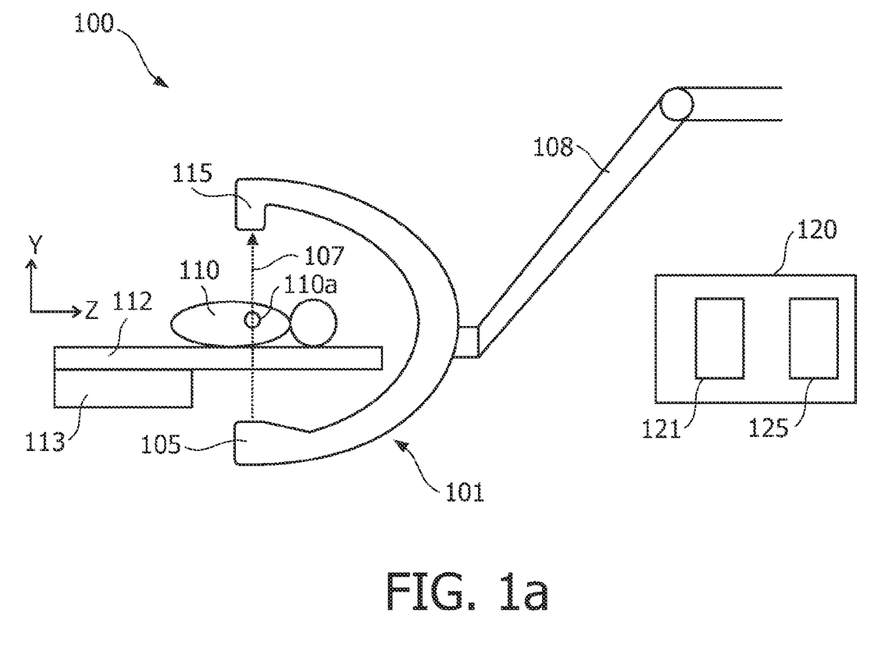
FIG. 1a shows a side view of a medical C-arm system, which is adapted to carry out a translative motion of an object under examination, wherein the translative motion is coupled to a rotational movement of the scanning unit.
Figure 1B:
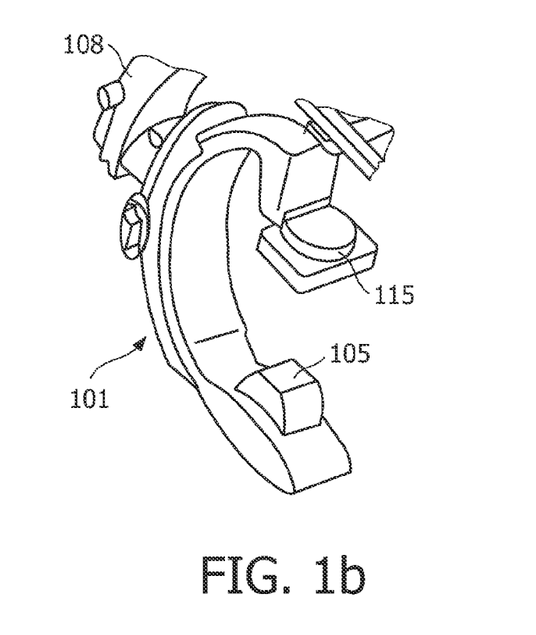

Referring to FIGS. 1a and 1b of the drawing, a medical X-ray imaging system 100 according to a further embodiment of the invention is a so called C-arm system. The C-arm system 100 comprises a swing arm scanning system 101 supported proximal a patient table 112 by a robotic arm 108. Housed within the swing C-arm 101, there is provided an X-ray scanning unit comprising an X-ray tube 105 and an X-ray detector 115. The X-ray detector 115 is arranged and configured to detect X-rays 107, which have passed through an object under examination 110. Typically, the object under examination is a patient 110.

The X-ray detector 115 is adapted to generate an electrical signal representative of the spatial intensity distribution of the detected X-rays 107 on the X-ray detector. By moving the swing arm 101, the X-ray tube 105 and the X-ray detector 115 can be placed at any desired angular orientation relative to the patient 110.

The C-arm system 100 further comprises a table drive means 113, which is adapted to move the table 112 along all three directions in space. Thereby, the patient 110 being supported by the table 112 may be positioned in the iso-center of the C-arm 101. It has to be mentioned that depending on a region of interest 110a within the patient's body, which may not be located in the center of the patient's body, the patient may be positioned slightly offset from the iso-center in order to allow that the region of interest 110a is located exactly in the iso-center.

However, if the region of interest 110a is not located in the center of the longitudinal axis of the patient 110, i.e. the region of interest 110a is shifted in the direction of an x-axis being perpendicular both to the depicted y-axis and the depicted z-axis, a collision between in particular the X-ray detector 115 and the patient's body might occur at some angular positions of the C-arm 101, when the region of interest 110a is located in the iso-center. Such a collision would restrict the possible angular range of the C-arm 101 movement. In order to increase this angular range the patient 110 is shifted predominately along the x-axis such that the region of interest 110a is temporarily positioned outside the iso-center and the body of the patient 110 as a whole is positioned at least approximately within the iso-center. This means that by coupling the rotational movement of the C-arm 101 with the translative movement of the patient 110 in a synchronized manner a collision between in particular the X-ray detector 115 and in particular a shoulder of the patient 110 can be effectively avoided.

Furthermore, the C-arm system 100 comprises a control unit 121 and a data processing device 125, which are both accommodated within a workstation or a personal computer 120. The control unit 121 is adapted to control both the rotational movement of the swing arm scanning system 101 and the translative motion of the table 112. The data processing device 125 is adapted for performing a three-dimensional (3D) reconstruction of the region of interest 110a based on a set of acquired X-ray attenuation data obtained at different angular positions of the C-arm 101.

Figure 2A:
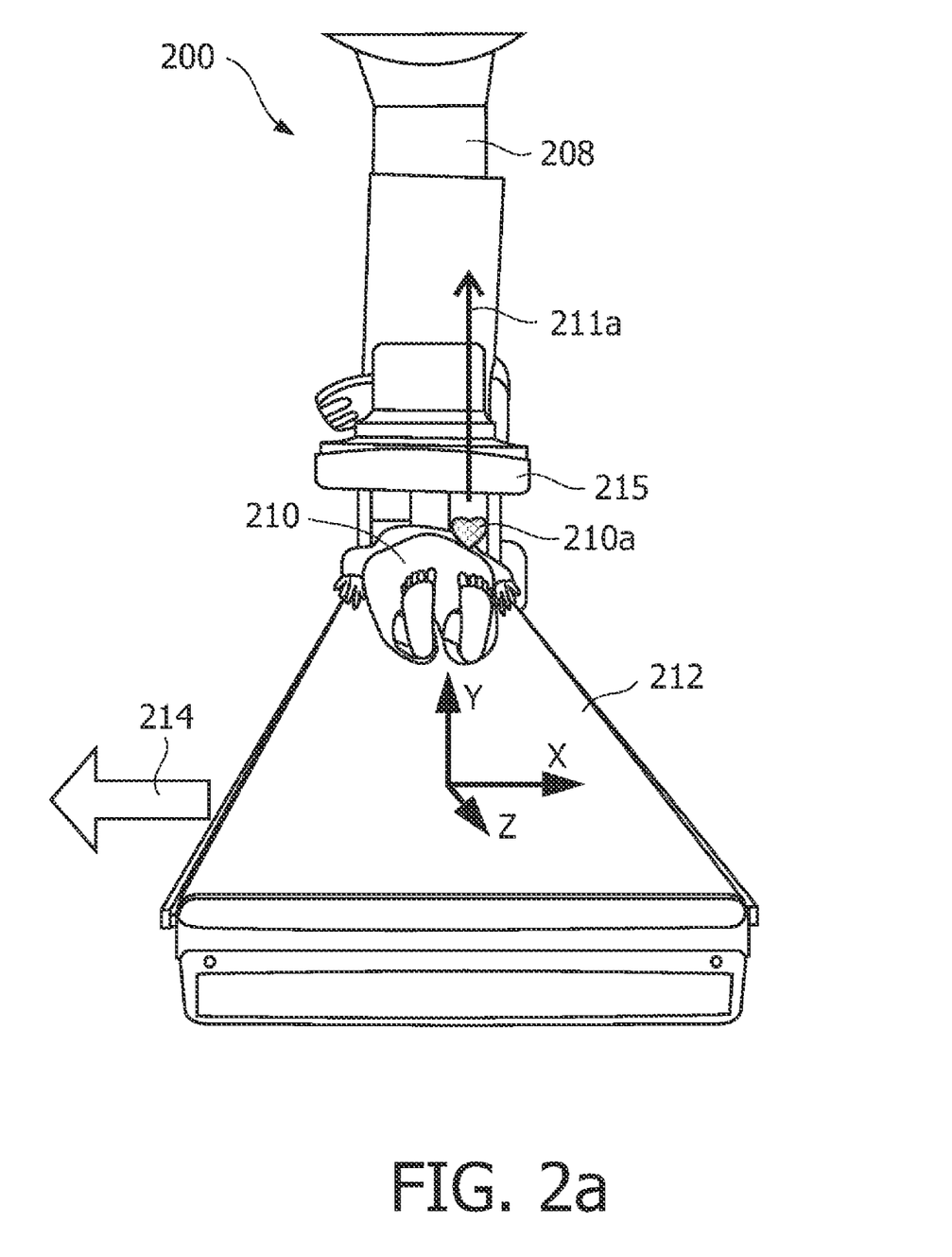
FIG. 2a shows a patient under examination positioned within a C-arm system, whereby the patient's body as a whole is positioned in the iso-center of the C-arm.

FIG. 2a shows a patient under examination 210 positioned within a C-arm system 200. The patient 210 is supported by a movable table 212, which table can be shifted along the x-axis, along the y-axis and along the z-axis. The C-arm system 200 comprises a robotic arm 208, at which a not visible C-arm is attached in a rotatable manner. A not visible X-ray source and an X-ray detector 215 are attached to the C-arm. The C-arm is capable of rotating around a z-axis such that the X-ray source and the X-ray detector 215 rotate around the patient 210 within a plane being oriented parallel to the x-axis as well as to the y-axis.

According to the embodiment described here the heart 210a of the patient 210 is examined. Since the heart 210a is located within the left side of the patient's body, the heart 210*a* will not be located in the iso-center of the C-arm if the patient's body as a whole is positioned within the iso-center. In FIG. 2*a* the offset positioning of the heart 210*a* with respect to the iso-center is indicated by the arrow 211*a*. The arrow 211*a* is not aligned with an optical axis of the X-ray detector 215. In order to move the region of interest 210*a* into the iso-center, the table 212 has to be moved along the x-axis in a negative direction i.e. to the left side. Such a table movement is indicated by the arrow 214.

Figure 2B:
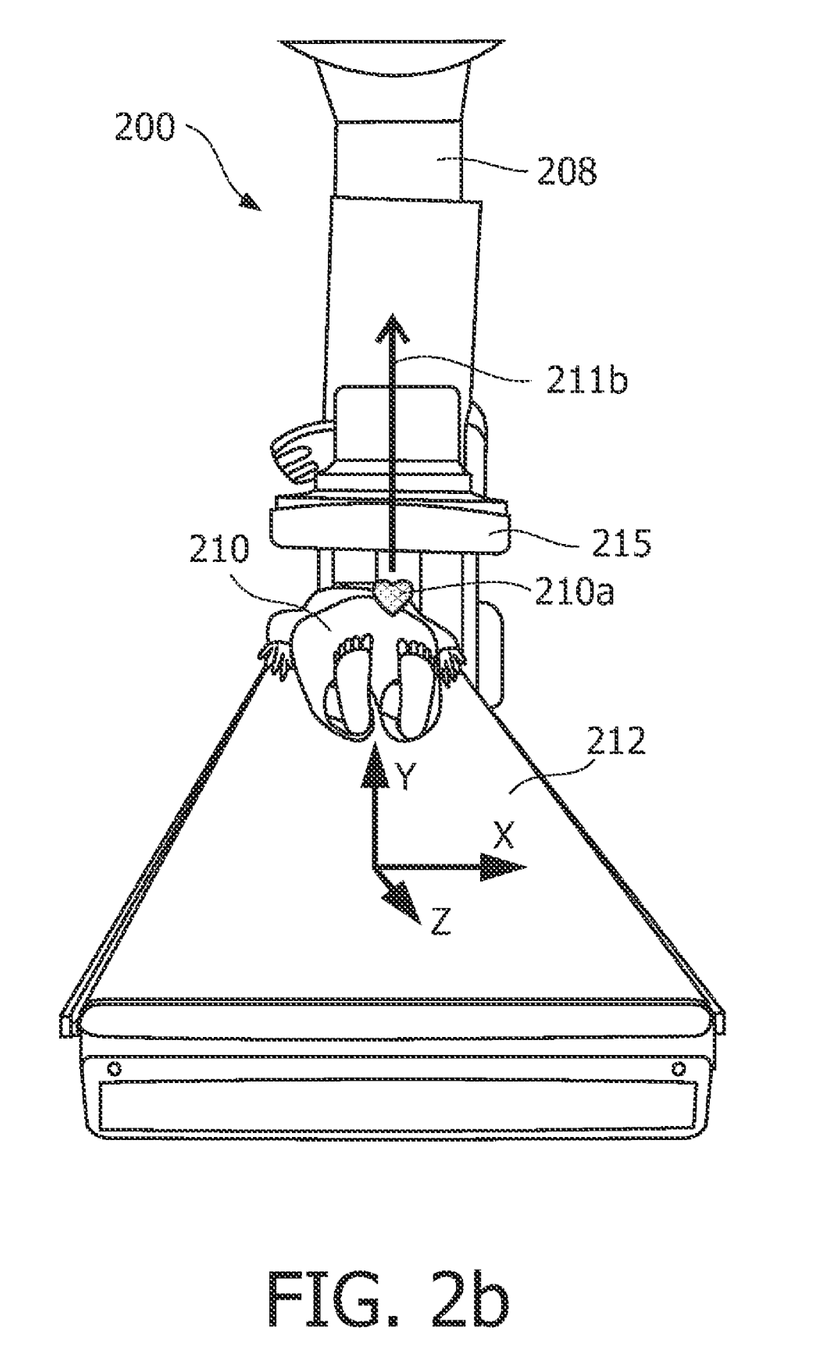
FIG. 2b shows the patient depicted in FIG. 2a in a position, whereby the patient's heart is positioned in the iso-center of the C-arm.

FIG. 2*b* shows the patient 210 within the C-arm system 200, whereby the patient's heart 210*a* is positioned in the iso-center. The iso-centering is indicated by the arrow 211*b*, which is aligned with the optical axis of the X-ray detector 215. In that case, the patient's body as a whole is shifted to the left compared to the iso-center of the C-arm.

FIGS. 3*a*-3*k* illustrate the combination of a rotational movement of a C-arm 301, which rotational movement is coupled in a synchronized manner with a horizontal movement of a patient table 312 in order to avoid a collision between an X-ray detector 315 of the C-arm 301 with a shoulder of the patient 310. The C-arm 301 is attached in a rotatable manner to a ceiling of an examination laboratory by means of a robotic arm 308.

Figure 3A:
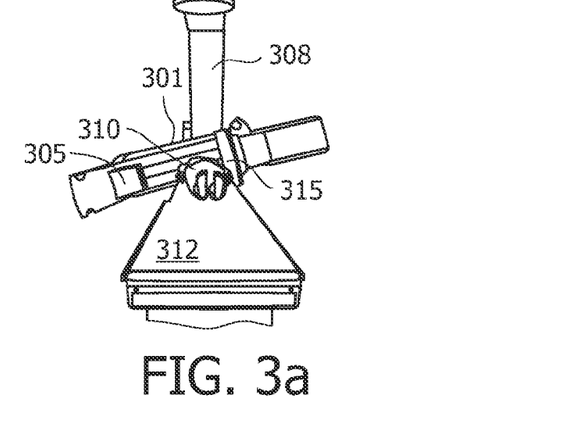
FIGS. 3a-3k illustrate the synchronized combination of a rotational movement of a C-arm with a horizontal movement of a patient table in order to avoid collisions between an X-ray detector of the C-arm with a shoulder of the patient.
Figure 3B:
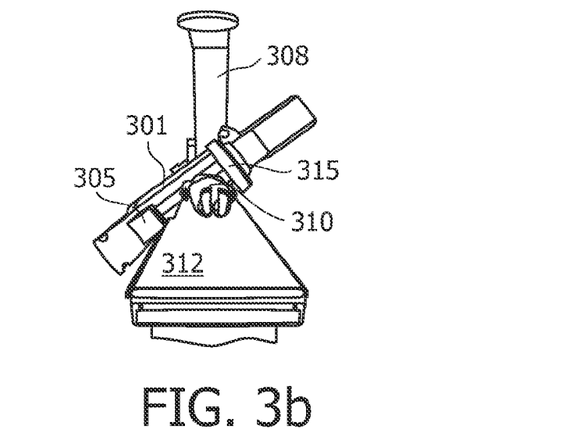
Figure 3C:
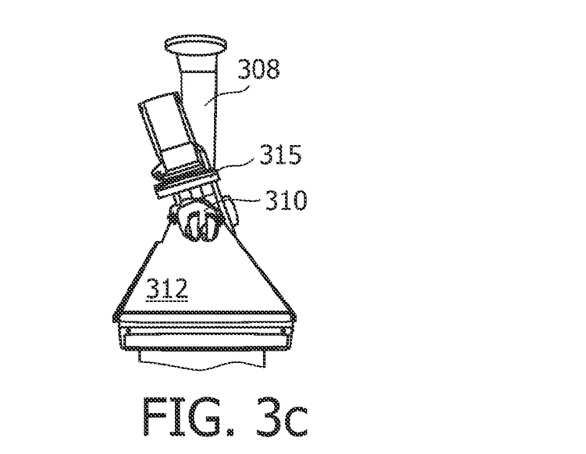

In the beginning of the rotational movement of the C-arm 301 the patient 310 is positioned in such a manner that the patient's heart is located in the iso-center of the C-arm 301. This situation is depicted in FIGS. 3*a*, 3*b* and 3*c*, which illustrate a first phase of the rotational movement of the C-arm 301. The C-arm 301 rotates in a counter-clockwise direction. Thereby, the X-ray source 305 of the C-arm 301 is moved in a rotatable manner underneath the patient 310. Consequently, the X-ray detector 315 is moved in a rotatable manner above the patient 310.

Figure 3D:
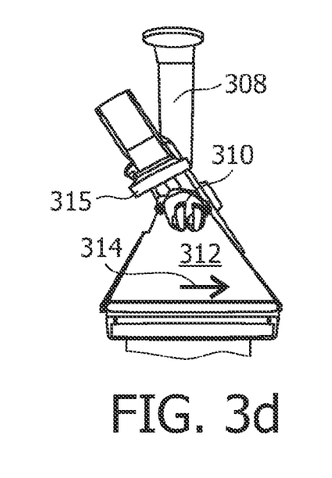
Figure 3E:
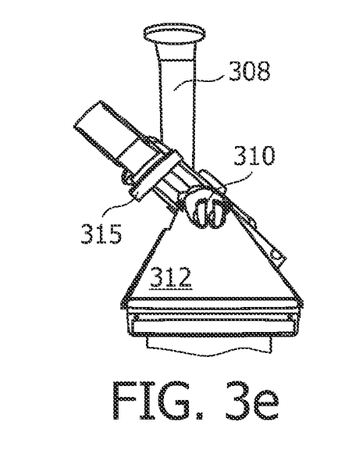
Figure 3F:
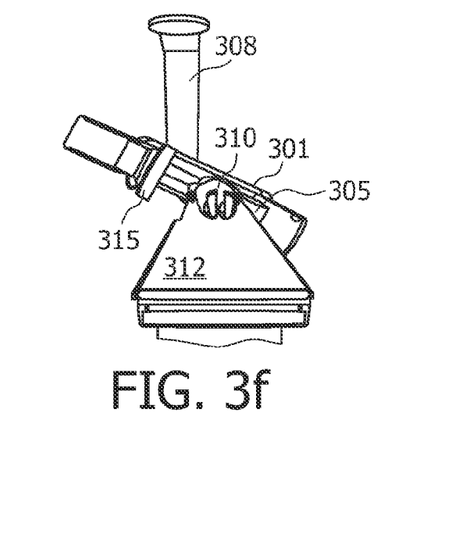
Figure 3G:
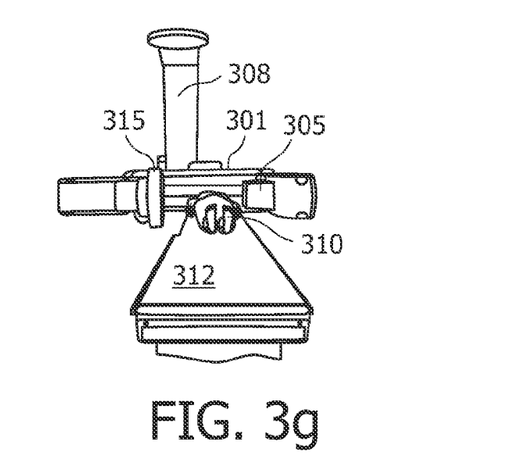
Figure 3H:
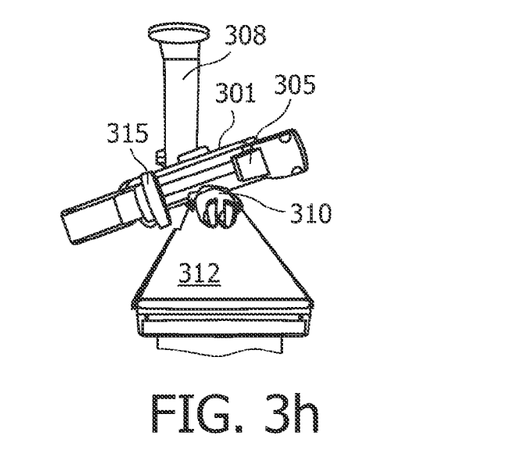
Figure 3I:
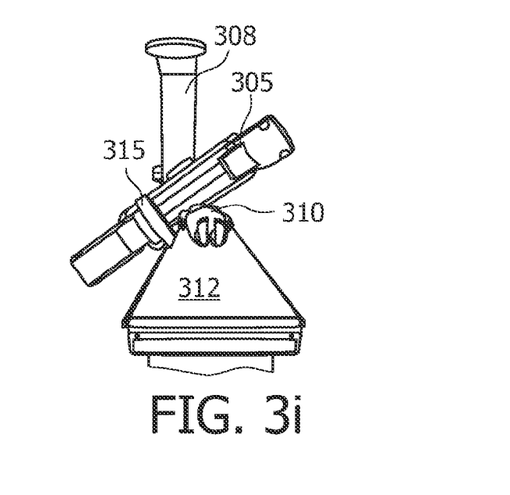

When the X-ray detector 315 approaches the right shoulder of the patient 310, the table 312 is shifted to the right such that the heart of the patient is offset from the iso-center. This table movement is indicated in FIG. 3*d* by the arrow 314*d*. Thereby, the right shoulder of the patient 310 is also moved to the right such that a collision between the X-ray detector 315 and the shoulder can be avoided. In other words, the accessible angular range of the C-arm 301 is increased such that further X-ray attenuation data may be acquired at more extreme projection angles.

As can be seen from FIGS. 3*e*, 3*f*, 3*g*, 3*h* and 3*i*, when the heart of the patient is located offset from the iso-center, the X-ray detector 315 of the C-arm 301 can be rotated around the shoulder of the patient 310 without having the risk of a collision.

Figure 3J:
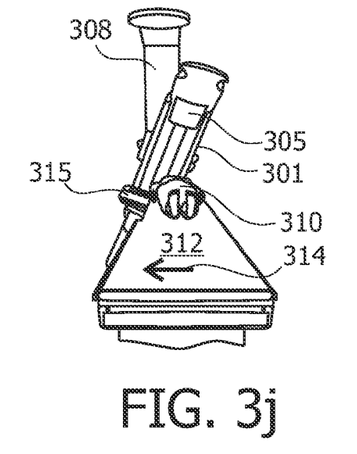

When the X-ray detector 315 is positioned below the shoulder, the table 312 is shifted back to its original position such that the patient's heart is again located in the iso-center of the C-arm 301. This table movement to the left is indicated in FIG. 3*j* by the arrow 314*f*.

Figure 3K:
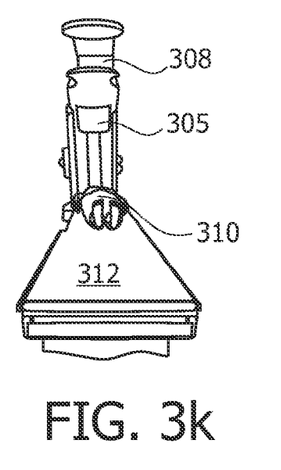

In order to complete a full cycle of the C-arm 301 the C-arm is further rotated to its original angular position. This situation is shown in FIG. 3*k*.

The intermediate table movement synchronized has the advantage, that the total accessible angular range can be increased in particular when thick patients are examined. By employing the described horizontal table movement the full angular range of a C-arm system can be exploited. For example the C-arm system FD20 Allura developed by Philips is capable of a C-arm propeller rotation from 120° left anterior oblique (LAO) to 185° right anterior oblique (RAO). Thereby, the projection angle is defined with respect to the view of a patient being positioned within the C-arm system.

Without employing the described horizontal table movement the C-arm system FD20 Allura cannot be used for cardiac applications because this full angular range cannot be used in particular for larger respectively thicker patients. Therefore, depending on the patient size, the C-arm movement would be limited to approximately 60° RAO only. Currently, the acquisition protocols for 3D coronary reconstruction require a C-arm propeller movement from 120° LAO to 60° RAO propeller movement.

In this respect it is pointed out that a rotation angle of 180° plus the angle of the beam spread of the X-ray beam is necessary in order to accomplish a 3D reconstruction procedure using known filtered back projection techniques.

By employing the described horizontal table movement it is possible to apply the acquisition protocols for 3D coronary reconstruction with currently available C-arm systems also for larger patients. Moreover, the above-mentioned C-arm system FD20 Allura has the ability to do extreme RAO projections that aid in the reconstruction process. Further, the described horizontal table movement unleashes capabilities already present but underutilized in currently available imaging systems, which capabilities are not limited to the reconstruction process. Furthermore, optimal view maps of coronary segments show that the acquisition of angular views between 60° RAO and 180° RAO are highly appreciated to generate projection images with a minimum of vessel shortening and vessel overlap. Such a reduced vessel shortening and vessel overlap increases the quality of two-dimensional (2D) angiograms and the resulting reconstructed and/or modeled 3D images significantly.

If a programmable and motorized patient table is available the above described horizontal table movement can carried out by executing the following steps:

1. Determination of an acquisition protocol for a rotational run acquisition. For example a 180° propeller rotation starting from 90° LAO to 90° RAO is appropriate.

2. Determination of the angular start point for the table shuttle movement. For example 30° LAO is appropriate.

3. Calibration of the C-arm rotational movement including the horizontal table movement.

4. Acquisition of patient data and if needed 3D reconstruction of the data after calibration.

Figure 4:
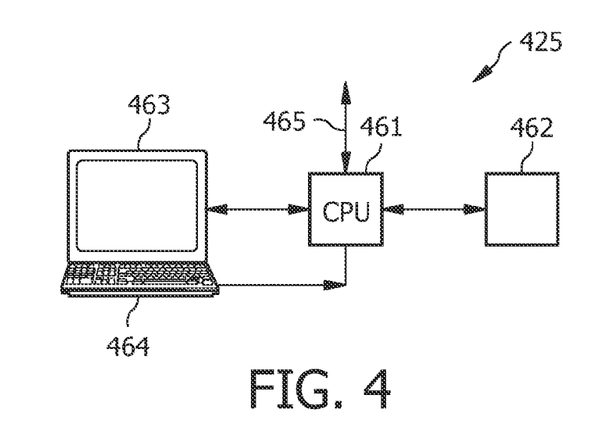
FIG. 4 shows a data processing device, which is adapted to perform an above-described method for acquiring a series of X-ray attenuation data of an object under examination by means of a rotatable X-ray scanning unit.

FIG. 4 shows a data processing device 425, which is adapted to perform an above-described method for acquiring a series of X-ray attenuation data of an object under examination by means of a rotatable X-ray scanning unit. The data processing device 425 comprises a central processing unit (CPU) or image processor 461. The image processor 461 is connected to a memory 462 for temporally storing acquired X-ray attenuation data. Via a bus system 465 the image processor 461 is connected to a plurality of input/output network or diagnosis devices of the C-arm system described above. Furthermore, the image processor 461 is connected to a display device 463, for example a computer monitor, for displaying information or one or more images reconstructed by the image processor 461. An operator or user may interact with the image processor 461 via a keyboard 464 and/or any other output devices, which are not depicted in FIG. 4.

It should be noted that the term "comprising" does not exclude other elements or steps and the "a" or "an" does not exclude a plurality. Also elements described in association with different embodiments may be combined. It should also be noted that reference signs in the claims should not be construed as limiting the scope of the claims.

In order to recapitulate the above described embodiments of the present invention one can state:

It is described a method for acquiring a series of two-dimensional X-ray attenuation data of an object under examination by means of an X-ray imaging apparatus having a rotatable scanning unit. In order to increase the angular range of the scanning unit, when a region of interest is examined, which region is located not in the center of the object but which region is originally positioned in the center of rotation of the scanning unit, the object under examination is shifted such that the region of interest is temporarily positioned outside the center of rotation. By coupling the rotational movement of the scanning unit with the translative movement of the object in a synchronized manner a collision between the scanning unit and the object can be effectively avoided. By employing an automated motorized object table a precise pre-determined movement of the object can be achieved during the data acquisition. By using an appropriate phantom based calibration procedure carried out with the same table movements known three-dimensional reconstruction algorithm can be directly applied in order to generate a three-dimensional representation of the region of interest.

LIST OF REFERENCE SIGNS 100 medical X-ray imaging system/C-arm system
101 X-ray scanning unit/swing arm scanning system/C-arm
105 X-ray source/X-ray tube
107 X-ray beam
108 robotic arm
110 object under examination/patient
112 table
113 table drive means
115 X-ray detector
120 workstation/personal computer
121 control unit
125 data processing device
200 C-arm system
208 robotic arm
210 object under examination/patient
210a region of interest/organ/heart
211a arrow indicating offset x-position of the heart
211b arrow indicating iso-centered x-position of the heart
212 table
214 arrow indicating table movement
215 X-ray detector
301 C-arm
305 X-ray source/X-ray tube
308 robotic arm
310 object under examination/patient
312 table
314d arrow indicating table movement to the right
314j arrow indicating table movement to the right
315 X-ray detector
425 data processing device
461 central processing unit/image processor
462 memory
463 display device
464 keyboard
465 bus system

The invention claimed is:

1. A method for acquiring a series of two-dimensional X-ray attenuation data of an object under examination that includes a region of interest by means of an X-ray imaging apparatus having an X-ray scanning unit, the method comprising the steps of
  positioning the object under examination to a first position, wherein the first position places the object such that a center of the object is off-set from an iso-center of the X-ray imaging apparatus and the region of interest is aligned with the iso-center of the X-ray imaging apparatus,
  rotating the X-ray scanning unit around a rotational axis such that the object under examination is scanned under different projection angles, and
  moving the object in a direction transverse to the rotational axis, to a second position, wherein the movement of the object is coupled to the rotation of the X-ray scanning unit and wherein the second position places the object such that the region of interest is not aligned with the iso-center of the X-ray imaging apparatus.

2. The method according to claim 1, further comprising the steps of
  rotating the X-ray scanning unit to a first predefined angular position while the object is in the first position,
  rotating the X-ray scanning unit to a second predefined angular position while the object is in the second position.

3. The method according to claim 2, further comprising the steps of
  moving the object under examination from the second position back to the first position, and
  further rotating the X-ray scanning unit.

4. The method according to claim 2, wherein
  the movement of the object under examination to the second position is carried out during a time period in which the rotation of the X-ray scanning unit is temporarily stopped.

5. The method according to claim 2, wherein
  the movement of the object under examination to the second position is carried out during a time period in which the X-ray scanning unit is rotated from the first predefined angular position to the second predefined angular position.

6. The method according to claim 1, wherein
  the object under examination is situated at a support element, which support element is coupled to a drive means for generating the movement of the object under examination from the first position to the second position.

7. The method according to claim 1, wherein
  the object under examination is at least a body of a patient.

8. The method according to claim 7, wherein
  the region of interest is an organ of the patient, which the organ is located off-center within the body of the patient, and wherein the organ is a heart of the patient.

9. The method according to claim 7, further comprising the step of
  inserting a contrast agent into the body of a patient.

10. The method according to claim 1, further comprising the step of
  reconstructing a three-dimensional representation of the object under examination based on the acquired series of two-dimensional X-ray attenuation data, whereby the movement, in the direction transverse to the rotational axis, of the object under examination is taken into account.

11. The method according to claim 1, further comprising the step of
  carrying out a calibration procedure for registering the movement of the object under examination with the rotation of the X-ray scanning unit.

12. A data processing device
for acquiring a series of two-dimensional X-ray attenuation data of an object under examination by means of an X-ray imaging apparatus having a rotatable X-ray scanning unit,
the data processing device comprising
a data processor, which is adapted for controlling the method as set forth in claim 1, and
a memory for storing the series of acquired two-dimensional X-ray attenuation data.

13. A medical X-ray imaging apparatus for acquiring a series of two-dimensional X-ray attenuation data of an object under examination, the medical X-ray imaging apparatus comprising
an X-ray scanning unit being rotatable around a rotational axis, wherein the X-ray scanning unit comprises
an X-ray source, which is adapted for emitting a radiation beam, and
an X-ray detector, which is adapted for detecting the radiation beam after the radiation beam has passed the object under examination,
a data processing device according to claim 12.

14. The medical X-ray imaging apparatus according to claim 13, further comprising
a support element for supporting the object under examination and
a drive means, which is coupled to the support element and which is configured to perform the moving the object under examination to the second position by moving the support element as the support element supports the object and is configured to perform the positioning the object to the first position by moving the support element as the support element supports the object under examination.

15. The medical X-ray imaging apparatus according to claim 14, further comprising
a control unit, which is coupled to the drive means and which is adapted to control the movement of the support element.

16. A computer-readable medium on which there is stored a computer program for acquiring a series of two-dimensional X-ray attenuation data of an object under examination by means of an X-ray imaging apparatus having a rotatable X-ray scanning unit,
the computer program, when being executed by a data processor, is adapted for controlling the method as set forth in claim 1.

17. A processor that executes a program element
for acquiring a series of two-dimensional X-ray attenuation data of an object under examination by means of an X-ray imaging apparatus having a rotatable X-ray scanning unit,
the program element, when being executed by the processor, is adapted for controlling the method as set forth in claim 1.

18. The method of claim 1, comprising:
identifying a potential collision between the object under examination and the X-ray scanning unit, wherein moving the object under examination to the second position occurs in response to identifying the potential collision.

19. The method of claim 18, wherein moving the object to the second position comprises moving the object such that the potential collision is avoided, wherein moving the object such that the potential collision is avoided is performed by physically moving a support that is supporting the object.

20. The method of claim 18, comprising:
identifying that the potential collision between the object and the X-ray scanning unit is avoided after moving the object to the second position; and
moving the object back to the first position, wherein the object under examination is scanned while the object is in the first position both times and while the object is in the second position, wherein moving the object back to the first position is performed by physically moving the support that is supporting the object and wherein positioning the object to a first position is performed by physically moving the support that is supporting the object.

* * * * *